(12) United States Patent
Damaj (10) Patent No.: US 11,000,527 B2
(45) Date of Patent: *May 11, 2021

(54) THERAPEUTIC METHODS AND COMPOSITIONS

(71) Applicant: INNOVUS PHARMACEUTICALS, INC., San Diego, CA (US)

(72) Inventor: Bassam Damaj, San Diego, CA (US)

(73) Assignee: INNOVUS PHARMACEUTICALS, INC., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/581,058

(22) Filed: Sep. 24, 2019

(65) Prior Publication Data

US 2020/0230143 A1 Jul. 23, 2020

Related U.S. Application Data

(63) Continuation of application No. 15/979,120, filed on May 14, 2018, now Pat. No. 10,456,401.

(60) Provisional application No. 62/505,514, filed on May 12, 2017.

(51) Int. Cl.

| | | |
|---|---|---|
| A61K 31/519 | (2006.01) | |
| A61K 47/12 | (2006.01) | |
| A61K 47/02 | (2006.01) | |
| A61K 47/38 | (2006.01) | |
| A61K 31/4525 | (2006.01) | |
| A61K 9/00 | (2006.01) | |
| A61P 15/10 | (2006.01) | |
| A61K 36/67 | (2006.01) | |
| A61K 45/06 | (2006.01) | |
| A61K 31/198 | (2006.01) | |

(52) U.S. Cl.
CPC .......... *A61K 31/519* (2013.01); *A61K 9/0014* (2013.01); *A61K 9/0053* (2013.01); *A61K 31/4525* (2013.01); *A61K 36/67* (2013.01); *A61K 45/06* (2013.01); *A61K 47/02* (2013.01); *A61K 47/12* (2013.01); *A61K 47/38* (2013.01); *A61P 15/10* (2018.01); *A61K 31/198* (2013.01); *A61K 2300/00* (2013.01)

(58) Field of Classification Search
CPC ................................................... A61K 31/519
See application file for complete search history.

(56) References Cited

U.S. PATENT DOCUMENTS

| | | | |
|---|---|---|---|
| 5,536,506 | A | 7/1996 | Majeed et al. |
| 5,744,161 | A | 4/1998 | Majeed et al. |
| 7,262,192 | B2 * | 8/2007 | Bell .................. A61P 11/02 514/234.2 |
| 9,161,565 | B1 | 10/2015 | Bezzek |
| 10,456,401 | B2 * | 10/2019 | Damaj .................. A61K 47/38 |
| 2001/0008641 | A1 | 7/2001 | Krotzer |
| 2008/0305096 | A1 | 12/2008 | Verdegem et al. |
| 2009/0143433 | A1 | 6/2009 | Hendrix |
| 2016/0106793 | A1 | 4/2016 | Peltier et al. |
| 2019/0167657 | A1 | 6/2019 | Damaj |

FOREIGN PATENT DOCUMENTS

| | | |
|---|---|---|
| EP | 0810868 | 8/2001 |
| EP | 2027857 | 2/2009 |
| WO | WO 2015/048590 | 4/2015 |
| WO | WO 2015/061860 | 5/2015 |

OTHER PUBLICATIONS

"All About Supplements—Pygeum," Life Extension, Apr. 2006, 5 pages [retrieved online Sep. 24, 2018 from: lifeextension.com/magazine/2006/4/aas/page-01].
"ASTRAGIN®," Nuliv Science, 2018, Product Insert, 2 pages [retrieved online from www.nulivscience.com].
CAS Registry, RN 94-62-2, Listing for Piperine, 1 pages, 1984.
"L-Arginine 500mg with Citrulline 250mg," Puritan's Pride, 2013, 3 pages.
"NuLiv Science announces self-affirmed GRAS for AstraGin ingredient," William Reed Business Media LTD, Mar. 25, 2012, last updated Mar. 15, 2017, 2 pages [retrieved online from: www.nutraingredients-usa.com/articles/2012/03/26nuliv-science-announces-self-affirmed-GRAS-for-AstraGin-ingredient].
"RECALMAX," Innovus Pharmaceuticals, Inc., Oct. 2016, Product Insert, 3 pages.
"Saw Palmetto," WebMD, 2018, 4 pages [retrieved online Sep. 27, 2018 from: www.webmd/com/vitamins/ai/ingredientmono-971/saw-palmetto].
"Vesele," Innovus Pharmaceuticals, Inc., Ot. 2016, Product Insert, 3 pages.
AWAD "Effect of beta-sitosterol, a plant sterol, on growth, protein phosphatase 2A, and phospholipase D in LLNCaP cells," Nutr. Cancer, 2000, vol. 36, No. 1, pp. 74-78 (abstract only).
Fry et al. "Impact of nitric-oxide-mediated vasodilation and oxidative stress on renal medullary oxygenation: modeling study," Am J Physiol Renal Physiol, 2016, vol. 310, pp. F237-F247.
Manukhina et al. "General Pathology and Pathophysiology. Role of Nitric Oxide in Prevention of Cognitive Disorders in Neurodegenerative Brain Infuries in Rats," Bulletin of Experimental Biology and Medicine, Oct. 2008, vol. 146, No. 4, pp. 391-395.
Mascio et al. "Lycopene as the most efficient biological carotenoid singlet oxygen quencher," Archives of Biochemistry and Biophysics, Nov. 1989, vol. 274, No. 2, pp. 532-538 (Abstract Only).
Mehmood et al. "Black Pepper and Piperine Possess Antidiarrheal Effect Mediated Through Phosphodiesterase Inhibitory and CA++ Antagonist Pathways," Basic & Clinical Pharmacology & Toxicology, 2014, vol. 115, Suppl. 1, p. 256, Abstract #834.
Morris, Jr. "Arginine Metabolism: Enzymology, Nutrition, and Clinical Significance, Enzymes of Arginine Metabolism," The Journal of Nutrition, Oct. 2004, vol. 134, No. 10, pp. 2743S-2747S.

(Continued)

*Primary Examiner* — Rei Tsang Shiao
(74) *Attorney, Agent, or Firm* — Sheridan Ross P.C.

(57) ABSTRACT

The invention provides compositions and methods that are effective to improve NO production in vivo and/or to increase NO levels in blood. Such compositions and methods may be useful to improve the effects of $PDE_5$ inhibitors, for example, on erectile dysfunction or pulmonary hypertension.

19 Claims, 5 Drawing Sheets

(56) References Cited

OTHER PUBLICATIONS

Morris, Jr. "Session I: Basic Aspects of Arginine Metabolism—Discussion Summary," The Journal of Nutrition, Oct. 2004, vol. 134, No. 10, pp. 2765S-2767S.
Mukhtar et al. "Green Tea in Chemoprevention of Cancer," Toxicological Sciences, 1999, vol. 52, Supplement, pp. 111-117.
Perva-Uzunalic et al. "Extraction of active ingredients from green tea (Camellia sinensis): Extraction efficiency of major catechins and caffeine," Food Chemistry, 2006, vol. 96, pp. 597-605.
Riehemann et al. "Plant extracts from stinging nettle (Urtica dioica), an antirheumatic remedy, inhibit the proinflammatory transcription factor NF-kappaB," FEBS Letters, 1999, vol. 442, pp. 89-94.
Simon et al. "Decoding the Substrate Supply to Human Neuronal Nitric Oxide Synthase," PLOSOne, Jul. 2013, vol. 8, No. 7, e67707, 12 pages.
International Search Report and Written Opinion for International (PCT) Patent Application No. PCT/US2018/032586, dated Jul. 4, 2018, 14 pages.
Official Action for U.S. Appl. No. 15/979,120, dated Nov. 30, 2018 15 pages.
Official Action for U.S. Appl. No. 15/979,120, dated May 17, 2019 8 pages.
Notice of Allowance for U.S. Appl. No. 15/979,120, dated Jun. 28, 2019 8 pages.
Nichols et al. "Pharmacokinetics of sildenafil citrate after single oral doses in healthy male subjects: absolute bioavailability, food effects and dose proportionality," British Journal of Clinical Pharmacology, Feb. 2002, vol. 53, No. S1, pp. 5S-12S.
Official Action for European Patent Application No. 18727979.9, dated Nov. 4, 2020 7 pages.

\* cited by examiner

Piperine Structure (2*E*,4*E*)-5-(benzo[*d*][1,3]dioxol-5-yl)-1-(piperidin-1-yl)penta-2,4-dien-1-one

Figure 4

Composition of Vesele® (diatary supplement) capsule

L-Citrulline    500mg
    L-Arginine    250 mg
    Bioperine    1.75 mg
    Other:    microcrystalline cellulose, silicon dioxide, and magnesium sterate or Composition of Vesele® (diatary supplement) capsule     L-Citrulline    500mg
    L-Arginine    250 mg
    Bioperine    5.0 mg
    Other:    microcrystalline cellulose, silicon dioxide, and magnesium sterate

Figure 5

THERAPEUTIC METHODS AND COMPOSITIONS

RELATED APPLICATION

This application is a continuation application of U.S. application Ser. No. 15/979,120 filed on May 14, 2018, which claims the benefit of priority of U.S. Provisional Application Ser. No. 62/505,514 filed on May 12, 2017, which applications are incorporated by reference herein.

BACKGROUND

Phosphodiesterase type 5 inhibitors ($PDE_5$ inhibitors) are agents that are used to block the action of cGMP-specific phosphodiesterase type 5 ($PDE_5$) on cyclic GMP. Currently, the $PDE_5$ inhibitors sildenafil, tadalafil, and vardenafil are clinically indicated for the treatment of erectile dysfunction, while sildenafil and tadalafil are also indicated for the treatment of pulmonary hypertension.

Figure 1:
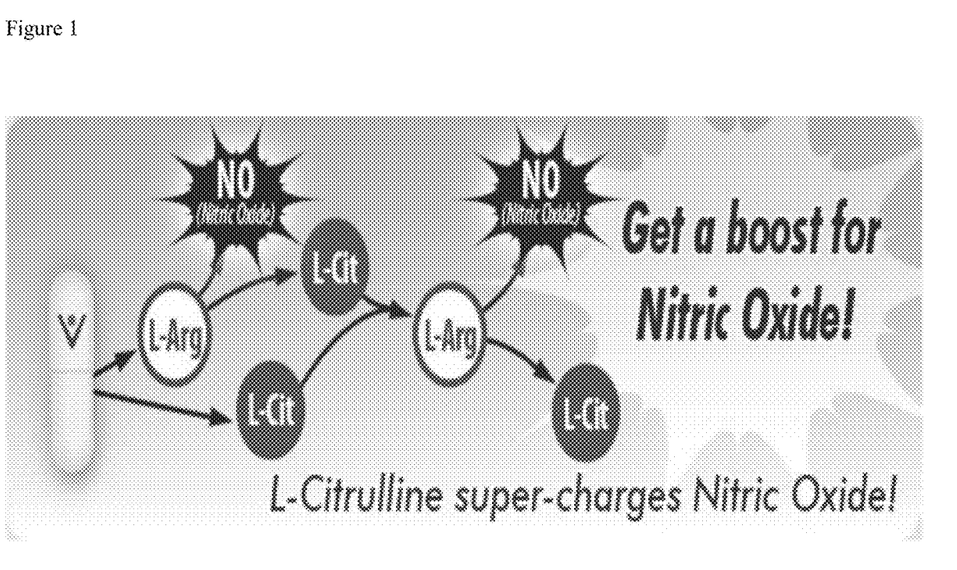
FIG. 1 shows the conversion of L-citrulline and L-argenine to NO.
Figure 2:
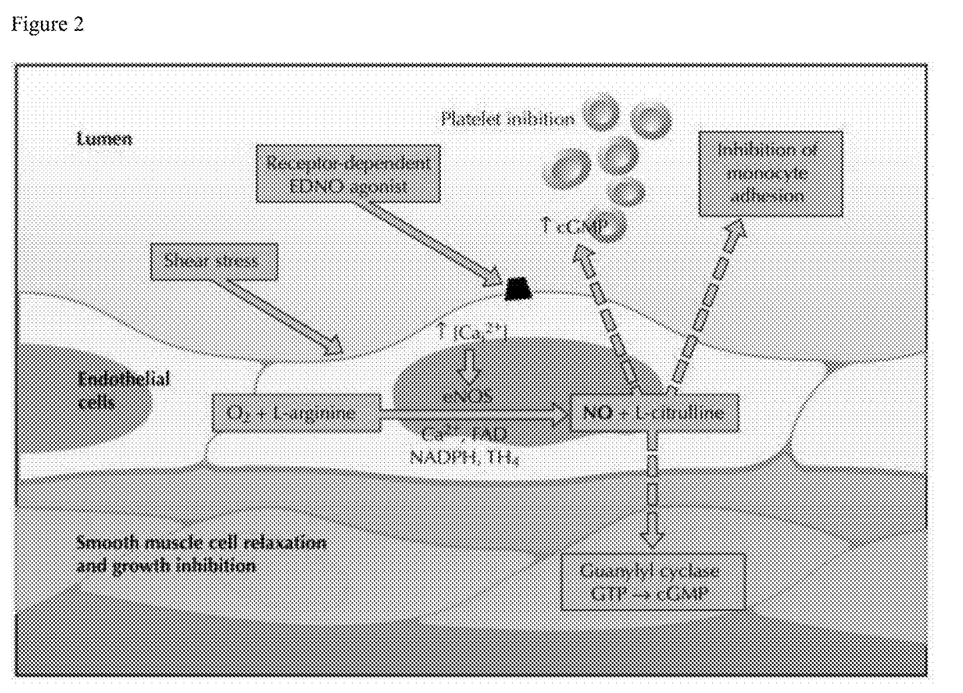
FIG. 2 shows how Nitric Oxide Synthase (NOS) in endothelial cells converts L-arginine to L-hydroxyarginine and subsequently to nitric oxide (NO) and L-citrulline.

Nitric Oxide Synthase (NOS) in endothelial cells converts L-arginine to L-hydroxyarginine and subsequently to nitric oxide (NO) and L-citrulline (FIG. 1 and FIG. 2). NO mediates its biological effects by activating guanylyl cyclase and increasing cyclic GMP synthesis from GTP which leads to the regulation of several biological processes such as vasodilation. 2 L-citrulline molecules combine to generate L-arginine to boost the NO generation cycle. NO exerts its biological action on smooth muscle by increasing cGMP which leads to vasodilation and increased blood flow in the genitals.

Figure 3:
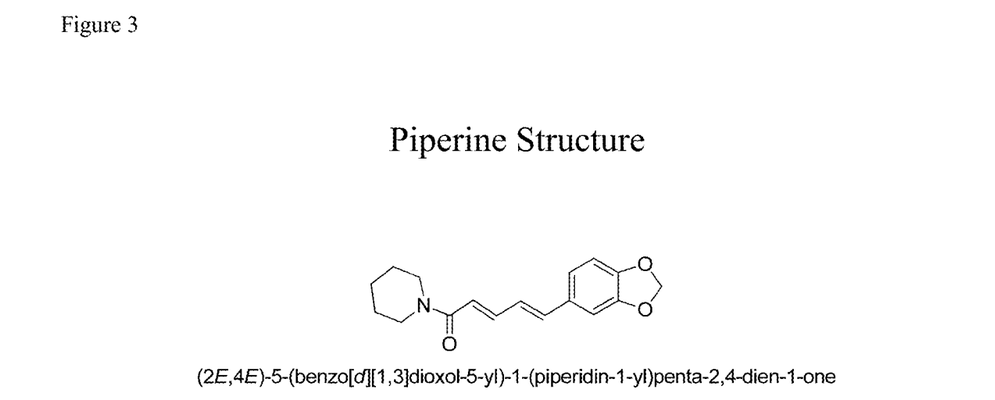
FIG. 3 shows the structure for Piperine.
Figure 4:
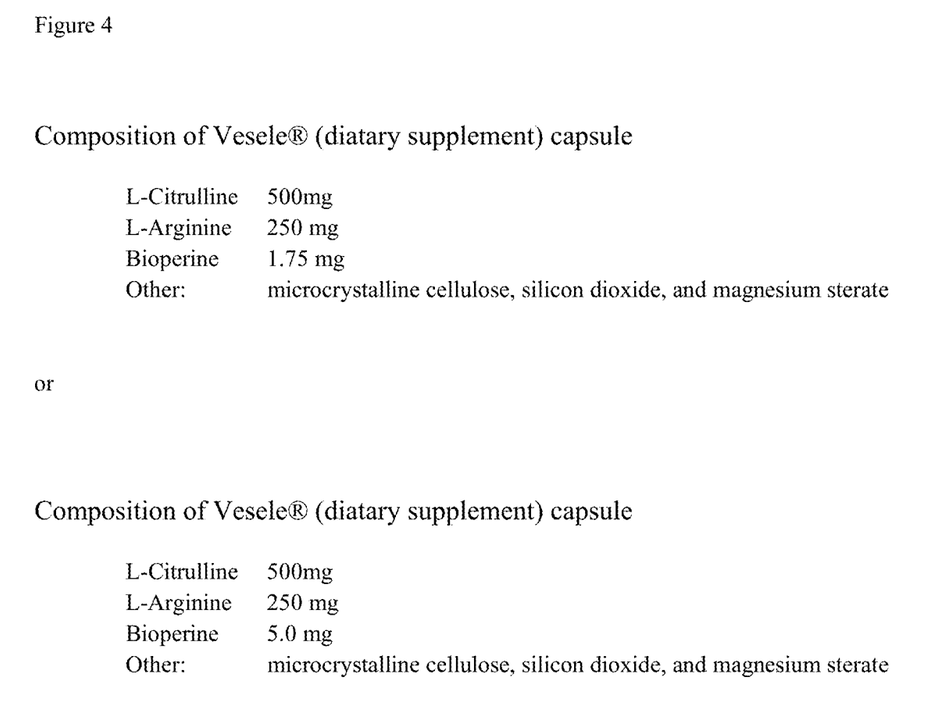
FIG. 4 shows the components of Vesele® (diatary supplement).
Figure 5:
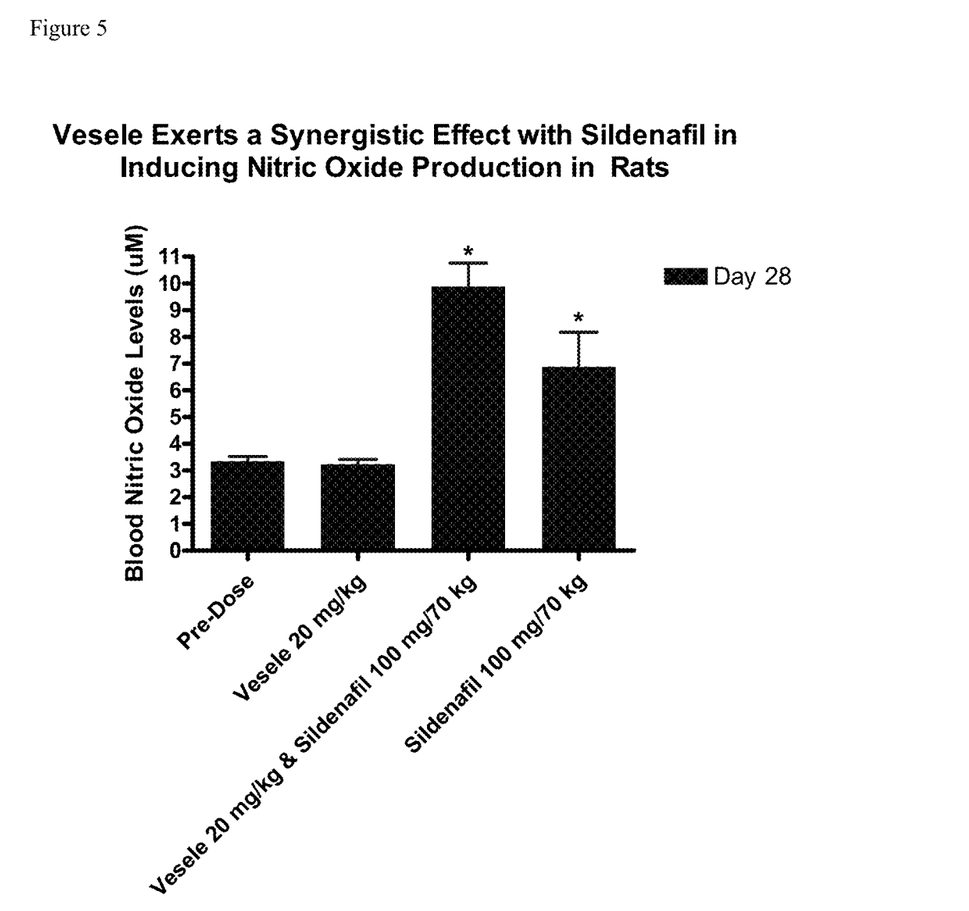
FIG. 5 shows data from Example 1.

Vesele® (diatary supplement) is a diatary supplement designed to maximize the benefits of NO. It contains the amino acids L-citruline and L-arginine, as well as BioPerine® (extract), a piperine (FIG. 3) extract that helps the body absorb the amino acids (see U.S. Pat. No. 5,536,506 and European Patent EP0810868B1). BioPerine® (extract) inhibits human CYP3A4 and P-glycoprotein enzymes. By inhibiting certain enzymes BioPerine® (extract) may alter the effectiveness of certain medications by increasing bioavailability. For men, daily consumption of Vesele® (diatary supplement) provides a significant improvement of erection hardness and maintenance, frequency of intercourse with partner and partner satisfaction as well as an overall satisfaction with sexual health. Women taking Vesele® (diatary supplement) have documented a significant satisfaction in lubrication, sexual desire, ability to be aroused and frequency of intercourse with partner.

In spite of the commercial success that sildenafil, tadalafil, and vardenafil have enjoyed, 50% of all patients stop using these drugs due to the lack of effect on erection and especially on penis hardness and maintenance to allow a successful vaginal penetration and ejaculation. There is currently a need for compositions and methods that are effective to improve and maintain NO production in vivo and/or to increase NO levels in blood to maintain an erection and maintain the hardness of the penis. There is also a need for improved compositions and methods that are effective to treat erectile dysfunction to continue to allow patients to respond properly to currnet treatments

SUMMARY

The invention provides compositions and methods that are effective to improve NO production in vivo and/or to increase NO levels in blood. Such compositions and methods may be useful to improve the effects of $PDE_5$ inhibitors, for example, on erectile dysfunction or pulmonary hypertension.

The invention provides a method to increase NO levels in the blood of a mammal comprising administering a $PDE_5$ inhibitor and piperine to the mammal.

The invention provides a method to treat erectile dysfunction in a mammal comprising administering a $PDE_5$ inhibitor and piperine to the mammal.

The invention provides a method to improve sexual function in a mammal comprising administering a $PDE_5$ inhibitor and piperine to the mammal.

The invention provides a method to improve cognitive function in a mammal comprising administering a $PDE_5$ inhibitor and piperine to the mammal.

The invention provides a method to improve erection hardness, erection maintenance, frequency of intercourse, partner satisfaction, or overall satisfaction with sexual health in a male human comprising administering a $PDE_5$ inhibitor and piperine to the male human.

The invention provides a method to improve lubrication, sexual desire, ability to be aroused or frequency of intercourse, in a female human comprising administering a $PDE_5$ inhibitor and piperine to the female human.

The invention provides a composition comprising piperine and a $PDE_5$ inhibitor.

The invention provides a $PDE_5$ inhibitor and piperine to increase NO levels in blood.

The invention provides a $PDE_5$ inhibitor and piperine to treat erectile function.

The invention provides a $PDE_5$ inhibitor and piperine to improve sexual function.

The invention provides a $PDE_5$ inhibitor and piperine to improve cognitive function.

The invention provides a $PDE_5$ inhibitor and piperine to improve sexual function.

The invention provides a $PDE_5$ inhibitor and piperine to improve erection hardness, erection maintenance, frequency of intercourse, partner satisfaction, or overall satisfaction with sexual health.

The invention provides a $PDE_5$ inhibitor and piperine to improve lubrication, sexual desire, ability to be aroused or frequency of intercourse.

DETAILED DESCRIPTION

In cases where compounds are sufficiently basic or acidic, a salt of a compound can be useful as an intermediate for isolating or purifying a compound. Additionally, administration of a compound as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, a-ketoglutarate, and a-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

In one embodiment the mammal is a human.

In one embodiment the $PDE_5$ inhibitor is sildenafil, tadalafil, or vardenafil or any other $PDE_5$ inihibitor.

In one embodiment the $PDE_5$ inhibitor is sildenafil, tadalafil, or vardenafil.

In one embodiment the $PDE_5$ inhibitor is sildenafil.

In one embodiment the piperine is synthetically produced piperine.

In one embodiment the piperine is an extract from the fruit of Piper.

In one embodiment the $PDE_5$ and the piperine are administered at the same time.

In one embodiment the $PDE_5$ and the piperine are administered at different times.

In one embodiment piperine is administered to the mammal before the $PDE_5$ inhibitor is administered to the mammal.

In one embodiment piperine is administered to the mammal in multiple doses over multiple days before the $PDE_5$ inhibitor is administered to the mammal.

In one embodiment a composition that comprising piperine and a $PDE_5$ inhibitor is administered to the mammal.

In one embodiment L-citruline is also administered to the mammal or human.

In one embodiment L-arginine is also administered to the mammal or human.

Animals: Wistar rats
Gender: male
Body weight: 120-150 g
Number of animals: 24
Study Duration: 4 weeks+1 week acclimation
Treatment: on day 1 T=0, animals were placed in treatment groups as indicated in the experimental grouping table.
Body Weight: was recorded prior dosing daily.
Observations: animals were observed daily for the duration of the study for overt clinical signs.
Blood collection: Blood was collected as per the time points indicated in the experimental grouping. Blood was split to generate serum for NO measurements and plasma for L-Arginine levels
Groups 1 and 2: Blood was collected as per the following time points:
D-1 of dosing, End of week 1, 2, 3 and 4 at 30 min post dose
Groups 3 and 4: blood was collected as per the following time points:
D-1 of dosing, at week 4 at 30 min post 30 min post dose
Total 84 samples.
Blood was collected in two tubes: One with coagulant for plasma and one without anticoagulant for serum. Tubes were transferred to the in vitro lab for processing.
Serum de-proteinization: Blood was allowed to coagulate at room temperature. Tubes were then centrifuged at room temperature and serum samples were separated by centrifugation using Thermo equipment. Samples were aliquoted into 2 tubes with a minimum of 35 uL/tube. Samples were then stored at −80° C. until ready for NO measurement.
Endpoint Analysis: samples were measured using the NO/Nitrite/Nitrate Assay: R&D Systems (Cat # KGE001). Each sample was run in duplicate wells at 1:2 dilution or additional as needed to be within the standard curve.

L-Arginine Levels in Plasma: L-Arginine Levels were Measured in Plasma by HPLC. The following experimental groupings were used.

| GROUP (n = 6/Group) | TREATMENT | DOSE (mg/Kg) | ROUTE | REGIMEN | Blood collection |
|---|---|---|---|---|---|
| 1 | Vehicle | N/A | PO | BID × 4 weeks | D-1 of dosing, End of week 1, 2, 3 and 4 at 30 min post each dose |
| 2 | Vesele ® (diatary supplement) | 20 | PO | BID × 4 weeks | |
| 3 | Vesele ® (diatary supplement) + Seldenafil | 100 mg/ 70 Kg | PO | BID × 4 weeks/ Seldenafil at T + 4 weeks | D-1 of dosing, At week 4 at 30 min post 30 min post each dose |
| 4 | Sildenafil | 100 mg/ 70 Kg | PO | At T + 4 weeks | |

The invention will now be illustrated by the following non-limiting Examples.

Example 1. Demonstration of the Synergistic Effect of Vesele® (Diatary Supplement) and Sildenafil on Nitric Oxide Production in Rats The following conditions were used to evaluate the effect of Vesele® (diatary supplement, 1.75 mg bioperine) and sildenafil on Nitric Oxide Production in Rats.

Data from Example 1 is shown in FIG. 1. The data demonstrates that the $PDE_5$ inhibitor sildenafil and Vesele® (diatary supplement) provide a synergistic effect on NO levels when administered together.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A method to increase NO levels in the blood of a mammal, treat erectile dysfunction in a mammal, improve sexual function in a mammal, or improve cognitive function in a mammal, comprising administering a $PDE_5$ inhibitor and piperine to the mammal.

2. A method to improve erection hardness, erection maintenance, frequency of intercourse, partner satisfaction, or overall satisfaction with sexual health in a male human or to improve lubrication, sexual desire, ability to be aroused or frequency of intercourse, in a female human, comprising administering a $PDE_5$ inhibitor and piperine to the human.

3. The method of claim 1 wherein the $PDE_5$ inhibitor is sildenafil, tadalafil, or vardenafil.

4. The method of claim 1 wherein the $PDE_5$ inhibitor is sildenafil.

5. The method of claim 1 wherein the piperine is synthetically produced piperine.

6. The method of claim 1 wherein the piperine is an extract from the fruit of Piper.

7. The method of claim 1 wherein the $PDE_5$ and the piperine are administered at the same time.

8. The method of claim 1 wherein the $PDE_5$ and the piperine are administered at different times.

9. The method of claim 1 wherein piperine is administered to the mammal before the $PDE_5$ inhibitor is administered to the mammal.

10. The method of claim 1 wherein piperine is administered to the mammal in multiple doses over multiple days before the $PDE_5$ inhibitor is administered to the mammal.

11. The method of claim 1 wherein a composition that comprises piperine and a $PDE_5$ inhibitor is administered to the mammal.

12. The method of claim 1 further comprising administering L-citrulline or L-arginine to the mammal.

13. The method of claim 1, further comprising administering L-citrulline and L-arginine to the mammal.

14. A composition comprising piperine and a $PDE_5$ inhibitor.

15. The composition of claim 14 wherein the $PDE_5$ inhibitor is sildenafil, tadalafil, or vardenafil.

16. The composition of claim 14 wherein the $PDE_5$ inhibitor is sildenafil.

17. The composition of claim 14 that is formulated for oral administration.

18. The composition of claim 14 that is formulated for topical administration.

19. The composition of claim 14, further comprising L-citrulline, L-arginine, microcrystalline cellulose, silicon dioxide, and magnesium stearate.

* * * * *